United States Patent

Gaino et al.

[11] 4,438,035
[45] Mar. 20, 1984

[54] METHOD OF PREPARING BENZOTHIAZEPINE DERIVATIVES

[75] Inventors: Mitsunori Gaino, Omiya; Ikuo Iijima, Urawa; Shigeru Nishimoto, Minoh; Kuichiro Ikeda, Onoda; Tokuo Fujii, Yamaguchi, all of Japan

[73] Assignee: Tanabe Seiyaku Co., Ltd., Osaka, Japan

[21] Appl. No.: 445,964

[22] Filed: Dec. 1, 1982

[30] Foreign Application Priority Data

Dec. 7, 1981 [JP] Japan .................................. 56-197358

[51] Int. Cl.³ .......................................... C07D 281/02
[52] U.S. Cl. .............................................. 260/239.3 B
[58] Field of Search .................................. 260/239.3 B

[56] References Cited

U.S. PATENT DOCUMENTS 3,562,257 2/1971 Kugita et al. ................. 260/239.3 B

OTHER PUBLICATIONS

Chemical and Engineering News, vol. 44, No. 15, p. 48, (1966).

*Primary Examiner*—Robert T. Bond
*Attorney, Agent, or Firm*—Jordan B. Bierman; Linda Bierman

[57] ABSTRACT

A benzothiazepine derivative of the formula:

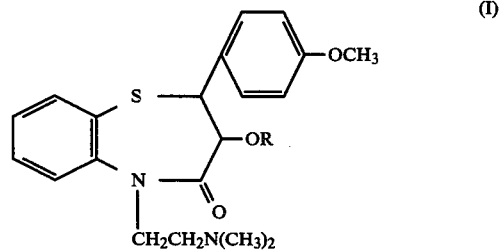

wherein R is hydrogen or acetyl, is prepared by condensing a compound of the formula:

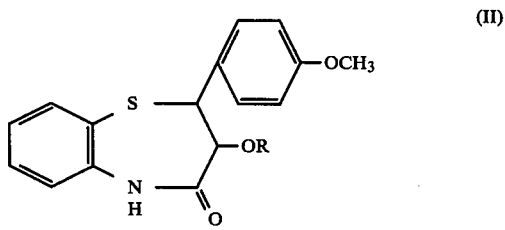

wherein R is the same as defined above, with 2-(dimethylamino)ethyl halide (i) in the presence of potassium hydroxide in acetone; or (ii) in the presence of potassium carbonate in acetone, lower alkyl acetate, a mixture of acetone and water or a mixture of lower alkyl acetate and water.

12 Claims, No Drawings

METHOD OF PREPARING BENZOTHIAZEPINE DERIVATIVES

This Application claims the priority of Japanese Application No. 197,358/1981, filed Dec. 7, 1981.

This invention relates to a novel method of preparing benzothiazepine derivatives. More particularly, it relates to a method of preparing benzothiazepine derivatives of the formula:

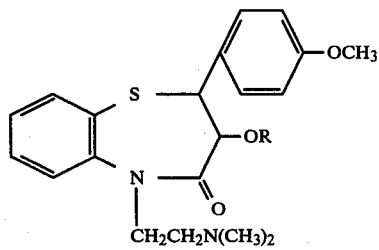

wherein R is hydrogen or acetyl, or a pharmaceutically acceptable acid addition salt thereof.

The benzothiazepine derivative (I) in which R is aetyl, especially cis-(+)-2-(4-methoxyphenyl)-3-acetoxy-5-[2-(dimethylamino)ethyl]-2,3-dihydro-1,5-benzothiazepine-4(5H)-one, is useful as a coronary vasodilator. On the other hand, the benzothiazepine derivative (I) in which R is hydrogen, especially cis-(+)-2-(4-methoxyphenyl)-3-hydroxy-5-[2-(dimethylamino)ethyl]-2,3-dihydro-1,5-benzothiazepine-4(5H)-one, is useful as an intermediate of the above-mentioned coronary vasodilator.

It is known that the benzothiazepine derivative (I) in which R is hydrogen is prepared by reacting 2-(4-methoxyphenyl)-3-hydroxy-2,3-dihydro-1,5-benzothiazepine-4(5H)-one with a base such as sodium hydride, metallic sodium or sodium amide in a solvent such as dimethylsulfoxide, dioxane, toluene or xylene, and then reacting the resultant sodium salt with 2-(dimethylamino)ethyl halide (U.S. Pat. No. 3,562,257). Moreover, in this method, sodium hydride and dimethylsulfoxide are known to be most suitable for use in carrying out said condensation reaction. However, the method of carrying out said condensation reaction by the use of sodium hydride and dimethylsulfoxide is still unsatisfactory in that said method is inevitably accompanied with side reactions due to methylsulfinylcarbanion ($CH_3SOCH_2^-$) which is formed during the reaction; and that sodium hydride is expensive and difficult to handle. Another disadvantage of the latter method is that, when sodium hydride is used in combination with dimethylsulfoxide, it is likely to explode. In fact, it has been reported that an explosion occurred when the alkylation of an aromatic heterocyclic compound was carried out by using sodium hydride and dimethylsulfoxide (Chem. Eng. News, 44(15), 48(1966)).

An object of the present invention is to provide a novel and improved method of preparing the benzothiazepine derivative (I). Another object of the invention is to provide a method of preparing the benzothiazepine derivative (I) without the accompanying disadvantages mentioned above. A further object of the invention is to provide a method of preparing the benzothiazepine derivative (I) by using potassium hydroxide or potassium carbonate which is inexpensive and easy to handle. These and other objects of the present invention will be apparent to persons skilled in the art from the following description.

According to the present invention, the benzothiazepine derivative (I) can be prepared by condensing a compound of the formula:

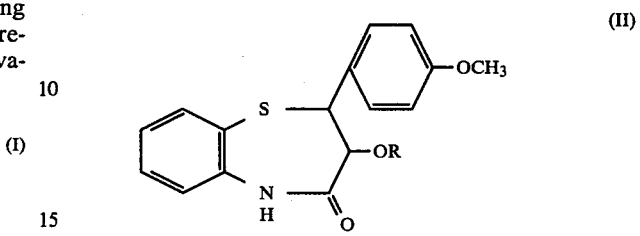

wherein R is the same as defined above, with 2-(dimethylamino)ethyl halide (III) either (i) in the presence of potassium hydroxide in acetone; or (ii) in the presence of potassium carbonate in a solvent selected from acetone, lower alkyl acetate, a mixture of acetone and water and a mixture of lower alkyl acetate and water.

It is preferred that 2-(dimethylamino)ethyl chloride, especially its hydrochloride, is used as the starting compound (III). On the other hand, suitable examples of the lower alkyl acetate include methyl acetate and ethyl acetate.

According to one embodiment of the present invention, the condensation of the compound (II) with the compound (III) is conducted in the presence of potassium hydroxide in acetone. A suitable amount of potassium hydroxide to be used in the above-mentioned reaction is 1 to 3 moles, especially 2 to 2.5 moles, per mole of the compound (II). On the other hand, a suitable amount of acetone is 5 to 30 ml, especially 5 to 15 ml, per gram of the compound (II). It is preferred that the mixture be stirred and that the reaction be carried out at a temperature between 30° C. and the refluxing temperature of acetone (i.e., at a temperature between 30° C. and 57° C.), especially at a temperature of 40° C. to 57° C. It is also preferred to carry it out in the presence of a dehydrating agent such as sodium sulfate because said dehydrating agent serves to increase the yield of the compound (I).

According to another embodiment of the present invention, the condensation of the compound (II) with the compound (III) is conducted in the presence of potassium carbonate in a solvent selected from the group consisting of acetone, lower alkyl acetate, a mixture of acetone and water and a mixture of lower alkyl acetate and water. A suitable amount of potassium carbonate to be used in the above-mentioned reaction is 1 to 5 moles, especially 2 to 3 moles, per mole of the starting compound (II). On the other hand, a suitable amount of the solvent (i.e., acetone, lower alkyl acetate, a mixture of acetone and water, a mixture of lower alkyl acetate and water) is 5 to 30 ml, especially 5 to 15 ml, per gram of the starting compound (II). It is preferred to carry out the reaction at a temperature between 30° C. and the refluxing temperature of the solvent used (i.e., at a temperature between 30° C. and 77° C.), especially under refluxing. Concomitantly, when the mixed solvent (i.e., a mixture of acetone and water or a mixture of lower alkyl acetate and water) is used as the solvent, it is preferred to carry out the reaction by refluxing a mixture of the compound (II), the compound (III), potassium carbonate and acetone or lower alkyl acetate, adding water to the mixture and then further refluxing the aqueous mixture. In this case, a suitable amount of water to be added is 0.01 to 0.1 ml per ml of acetone or lower alkyl acetate.

While the starting compound (II) of the present invention can exist in the form of two stereoisomers (i.e., cis- and trans-isomers) and each one of said stereoisomers can exist further in the form of two optical isomers (i.e., d- and l-isomers), all of these isomers or a mixture thereof can be used in the method of the present invention to give the corresponding isomers of the compound (I) or a mixture thereof.

The thus obtained compound (I) can be converted into a pharmaceutically acceptable acid addition salt thereof by treating said compound with an inorganic acid or organic acid (e.g., hydrochloric acid, hydrobromic acid, sulfuric acid, nitric acid, perchloric acid, acetic acid, oxalic acid, malonic acid, tartaric acid, malic acid, citric acid, lactic acid) in a solvent (e.g., water, methanol, ethanol).

As mentioned hereinbefore, in comparison with the known method disclosed in U.S. Pat. No. 3,562,257 (e.g., a method of preparing the benzothiazepine derivative (I) by the use of sodium hydride and dimethylsulfoxide), the above-mentioned method of the present invention is quite advantageous and economical for preparing the benzothiazepine derivative (I) on an industrial scale because the benzothiazepine (I) can be prepared without undesirable side reactions by the use of such an inexpensive reagent as potassium hydroxide or potassium carbonate. Moreover, since the potassium hydroxide or potassium carbonate to be used in the present invention is quite stable and easy to handle, the method of the present invention can be carried out without explosive accidents as reported in Chem. Eng. News, 44, 48(1966).

Practical and presently preferred embodiments of the present invention are illustratively shown in the following Examples. Throughout the specification and claims, the term "lower alkyl" should be interpreted as referring to alkyl having one to four carbon atoms.

EXAMPLE 1

A mixture of 30.1 g of cis-(+)-2-(4-methoxyphenyl)-3-hydroxy-2,3-dihydro-1,5-benzothiazepine-4(5H)-one, 17.8 g of 2-(dimethylamino)ethyl chloride hydrochloride, 13.7 g of 96% potassium hydroxide, 60 g of sodium sulfate and 300 ml of acetone is stirred at 50° C. for 7 hours. After the reaction is completed, the mixture is filtered to remove inorganic materials and the filtrate is condensed. The residue is dissolved in ethanol. After cooling the solution, 10% HCl/ethanol is added thereto. The crystalline precipitates are collected by filtration and then dried. 35.1 g of cis-(+)-2-(4-methoxyphenyl)-3-hydroxy-5-[2-(dimethylamino)ethyl]-2,3-dihydro-1,5-benzothiazepine-4(5H)-one hydrochloride are thereby obtained. Yield: 86.2%

M.p. 225°–227° C. (decomp.)

EXAMPLE 2

A mixture of 30.1 g of cis-(+)-2-(4-methoxyphenyl)-3-hydroxy-2,3-dihydro-1,5-benzothiazepine-4(5H)-one, 17.2 g of 2-(dimethylamino)ethyl chloride hydrochloride, 31.8 g of potassium carbonate and 240 ml of acetone is refluxed for 30 minutes after stirring. Then, 10 ml of water are added to the mixture, and the aqueous mixture is further refluxed for 3 hours under stirring. After the reaction is completed, the mixture is evaporated under reduced pressure to remove acetone. The residue is dissolved in toluene, and the solution is washed twice with water. The toluene layer is collected and then evaporated under reduced pressure to remove toluene. The residue is dissolved in ethanol. After cooling the solution, said solution is acidified with 10% HCl/ethanol and then stirred at a temperature below 5° C. for 5 hours. The crystalline precipitates are collected by filtration, washed with ethanol and then dried. 37.1 g of cis-(+)-2-(4-methoxyphenyl)-3-hydroxy-5-[2-(dimethylamino)ethyl]-2,3-dihydro-1,5-benzothiazepine-4(5H)-one hydrochloride are thereby obtained. Yield: 90.7%

M.p. 225°–227° C. (decomp.)

EXAMPLE 3

A mixture of 30.1 g of cis-(+)-2-(4-methoxyphenyl)-3-hydroxy-2,3-dihydro-1,5-benzothiazepine-4(5H)-one, 18.7 g of 2-(dimethylamino)ethyl chloride hydrochloride, 33.0 g of potassium carbonate and 240 ml of ethyl acetate is refluxed for 30 minutes under stirring. Then, 5 ml of water are added to the mixture, and the aqueous mixture is further refluxed for 6 hours under stirring. After cooling the reaction mixture, said mixture is washed with water. The ethyl acetate layer is separated and washed with water. The ethyl acetate layer is then evaporated under reduced pressure to remove ethyl acetate. The residue is dissolved in ethanol. After cooling the solution, said solution is acidified with 10% HCl/ethanol and then stirred at a temperature below 10° C. for 5 hours. The crystalline precipitates are collected by filtration, washed with ethanol and then dried. 37.9 g of cis-(+)-2-(4-methoxyphenyl)-3-hydroxy-5-[2-(dimethylamino)ethyl]-2,3-dihydro-1,5-benzothiazepine-4(5H)-one hydrochloride are thereby obtained. Yield: 92.7%

M.p. 225°–227° C. (decomp.)

EXAMPLE 4

To a mixture of 30.1 g of cis-(+)-2-(4-methoxyphenyl)-3-hydroxy-2,3-dihydro-1,5-benzothiazepine-4(5H)-one, 34.5 g of powdery potassium carbonate and 300 ml of acetone are added 18.7 g of 2-(dimethylamino)ethyl chloride hydrochloride at room temperature under stirring. The mixture is refluxed for 9 hours under stirring. After cooling the mixture, said mixture is evaporated to remove acetone. The residue is dissolved in ethyl acetate, and the solution is washed with water, dried and then evaporated to remove ethyl acetate. The residue is dissolved in methanol. After cooling the solution, said solution is acidified with 10% HCl/ethanol and then evaporated to remove solvent. The residue is recrystallized from isopropanol, whereby 38.64 g of cis-(+)-2-(4-methoxyphenyl)-3-hydroxy-5-[2-(dimethylamino)ethyl]-2,3-dihydro-1,5-benzothiazepine-4(5H)-one hydrochloride are obtained. Yield: 94.5%

M.p. 225°–227° C. (decomp.)

EXAMPLE 5

To a mixture of 30.1 g of cis-(+)-2-(4-methoxyphenyl)-3-hydroxy-2,3-dihydro-1,5-benzothiazepine-4(5H)-one, 34.5 g of powdery potassium carbonate and 300 ml of ethyl acetate are added 18.7 g of 2-(dimethylamino)ethyl chloride hydrochloride at room temperature under stirring. The mixture is refluxed for 23 hours under stirring. After cooling the mixture, said mixture is washed with water, dried and then evaporated to remove ethyl acetate. The residue is dissolved in methanol. After cooling the solution, said solution is acidified with 10% HCl/ethanol and then evaporated to remove solvent. The residue is recrystallized from isopropanol, whereby 36.8 g of cis-(+)-2-(4-methoxyphenyl)-3-hydroxy-5-[2-(dimethylamino)ethyl]-2,3-dihydro-1,5-benzothiazepine-4(5H)-one hydrochloride are obtained. Yield: 90.2%

M.p. 225°-227° C. (decomp.)

EXAMPLE 6

To a mixture of 3.43 g of cis-(+)-2-(4-methoxyphenyl)-3-acetoxy-2,3-dihydro-1,5-benzothiazepine-4(5H)-one, 3.45 g of powdery potassium carbonate and 30 ml of acetone are added 1.87 g of 2-(dimethylamino)-chloride hydrochloride at room temperature under stirring. The mixture is refluxed for 7.5 hours. After cooling the reaction mixture, said mixture is filtered to remove inorganic materials, and the filtrate is condensed under reduced pressure. The residue is dissolved in chloroform. After cooling the solution, said solution is adjusted to pH 3 with 10% HCl/ethanol. The chloroform solution is washed with an aqueous saturated sodium chloride solution, dried and then condensed under reduced pressure. The residue is dissolved in isopropanol under heating, and the solution is cooled. The crystalline precipitates are collected by filtration, whereby 4.06 g of cis-(+)-2-(4-methoxyphenyl)-3-acetoxy-5-[2-(dimethylamino)ethyl]-2,3-dihydro-1,5-benzothiazepine-4(5H)-one hydrochloride are obtained. Yield: 90%

M.p. 205°-207° C. (decomp.)

$[\alpha]_D^{27} = +96.6°$ (C=0.61, methanol)

EXAMPLE 7

A mixture of 30.1 g of cis-(+)-2-(4-methoxyphenyl)-3-hydroxy-2,3-dihydro-1,5-benzothiazepine-4(5H)-one, 32.0 g of potassium carbonate, 18.7 g of 2-(dimethylamino)ethyl chloride hydrochloride and 240 ml of methyl acetate is refluxed for 30 minutes under stirring. Then, 7.5 ml of water are added dropwise to the mixture, and said mixture is further refluxed for 30 hours under stirring. After cooling the reaction mixture, said mixture is poured into 150 ml of water. The aqueous layer is extracted with methyl acetate, and the extract is combined with the methyl acetate layer. The combined solution is washed twice with water and then evaporated to remove methyl acetate. The residue is dissolved in ethanol. After cooling the solution, said solution is acidified with 10% HCl/ethanol and then cooled to a temperature below 10° C. The crystalline precipitates are collected by filtration, whereby 35.7 g of cis-(+)-2-(4-methoxyphenyl)-3-hydroxy-5-[2-(dimethylamino)ethyl]-2,3-dihydro-1,5-benzothiazepine-4(5H)-one hydrochloride are obtained. Yield: 87.3%

M.p. 225°-227° C. (decomp.)

PREPARATION (Synthesis of the starting compound)

30 ml of pyridine are added to 6 g of cis-(+)-2-(4-methoxyphenyl)-3-hydroxy-2,3-dihydro-1,5-benzothiazepine-4(5H)-one, and the mixture is cooled with ice-water. 1.77 g of acetyl chloride are added dropwise to the mixture under stirring, and said mixture is allowed to stand in a refrigerator overnight. Then, the mixture is poured into about 600 ml of ice-water, and the precipitated crystals are collected by filtration. The crystals are washed with water, 2% hydrochloric acid and water, successively. Then, said crystals are recrystallized from ethanol, whereby 4.06 g of cis-(+)-2-(4-methoxyphenyl)-3-acetoxy-2,3-dihydro-1,5-benzothiazepine-4(4H)-one are obtained as colorless needles. Yield: 71%

M.p. 151°-152° C. (decomp.)

$[\alpha]_D^{20} = +35.48°$ (C=1.03, CHCl3)

What we claim is:

1. A method of preparing a benzothiazepine derivative of the formula:

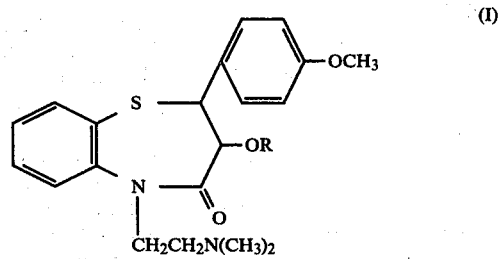

wherein R is hydrogen or acetyl, or a pharmaceutically acceptable acid addition salt thereof, which comprises condensing a compound of the formula:

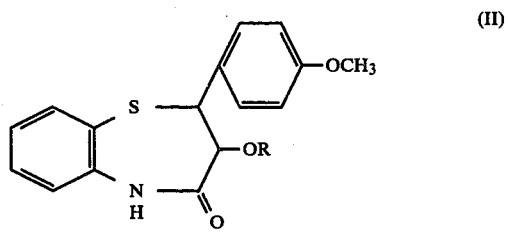

wherein R is the same as defined above, with 2-(dimethylamino)ethyl halide either in the presence of potassium hydroxide in acetone or in the presence of potassium carbonate in a solvent selected from acetone, lower alkyl acetate, a mixture of acetone and water and a mixture of lower alkyl acetate and water, and if required, further converting the product into a pharmaceutically acceptable acid addition salt thereof.

2. The method according to claim 1, wherein the condensation is carried out either in the presence of 1 to 3 moles of potassium hydroxide per mole of the compound (II) in acetone at a temperature between 30° C. and the refluxing temperature of acetone or in the presence of 1 to 5 moles of potassium carbonate per mole of the compound (II) in a solvent selected from acetone, lower alkyl acetate, a mixture of acetone and water and a mixture of lower alkyl acetate and water at a temperature of 30° C. and the refluxing temperature of the solvent used.

3. The method according to claim 1, wherein, when potassium hydroxide and acetone are used, the condensation is carried out by stirring a mixture of the compound (II), 2-(dimethylamino)ethyl chloride, potassium hydroxide and acetone at a temperature of 40° C. to 57° C.; when potassium carbonate and acetone or lower alkyl acetate are used, the condensation is carried out by refluxing a mixture of the compound (II), 2-(dimethylamino)ethyl chloride, potassium carbonate and acetone or lower alkyl acetate; when potassium carbonate and a mixture of acetone and water or a mixture of lower alkyl acetate and water are used, the condensation is carried out by refluxing a mixture of the compound (II), 2-(dimethylamino)ethyl chloride, potassium carbonate and acetone or lower alkyl acetate, adding water to the mixture and then further refluxing the aqueous mixture.

4. The method according to claim 1, wherein the lower alkyl acetate is methyl acetate or ethyl acetate.

5. The method according to claim 3, wherein the lower alkyl acetate is methyl acetate or ethyl acetate.

6. The method according to claim 3, wherein 2-(dimethylamino)ethyl chloride is used in the form of its hydrochloride.

7. The method according to claim 6, wherein the amount of potassium hydroxide is 2 to 2.5 moles per mole of the compound (II), and the amount of potassium carbonate is 2 to 3 moles per mole of the compound (II).

8. The method according to claim 2, wherein, when potassium hydroxide and acetone are used, the condensation is carried out by stirring a mixture of the compound (II), 2-(dimethylamino)ethyl chloride, potassium hydroxide and acetone at a temperature of 40° C. to 57° C.; when potassium carbonate and acetone or lower alkyl acetate are used, the condensation is carried out by refluxing a mixture of the compound (II), 2-(dimethylamino)ethyl chloride, potassium carbonate and acetone or lower alkyl acetate; when potassium carbonate and a mixture of acetone and water or a mixture of lower alkyl acetate and water are used, the condensation is carried out by refluxing a mixture of the compound (II), 2-(dimethylamino)ethyl chloride, potassium carbonate and acetone or lower alkyl acetate, adding water to the mixture and then further refluxing the aqueous mixture.

9. The method according to claim 2, wherein the lower alkyl acetate is methyl acetate or ethyl acetate.

10. The method according to claim 8, wherein the lower alkyl acetate is methyl acetate or ethyl acetate.

11. The method according to claim 8, wherein 2-(dimethylamino)ethyl chloride is used in the form of its hydrochloride.

12. The method according to claim 11, wherein the amount of potassium hydroxide is 2 to 2.5 moles per mole of the compound (II), and the amount of potassium carbonate is 2 to 3 moles per mole of the compound (II).

* * * * *

REEXAMINATION CERTIFICATE (2342nd)
United States Patent
[19]

Gaino et al.

[11] B1 4,438,035

[45] Certificate Issued  Jul. 26, 1994

[54] METHOD OF PREPARING BENZOTHIAZEPINE DERIVATIVES

[75] Inventors: Mitsunori Gaino, Omiya; Ikuo Iijima, Urawa; Shigeru Nishimoto, Minoh; Kuichiro Ikeda, Onoda; Tokuo Fujii, Yamaguchi, all of Japan

[73] Assignee: Tanabe Seiyaku Co., Ltd., Japan

Reexamination Requests:
No. 90/003,349, Mar. 1, 1994
No. 90/003,044, May 5, 1993

Reexamination Certificate for:
Patent No.: 4,438,035
Issued: Dec. 1, 1982
Appl. No.: 445,964
Filed: Dec. 12, 1982

[30] Foreign Application Priority Data

Dec. 7, 1981 [JP]  Japan ................ 56-197358

[51] Int. Cl.$^5$ ............................... C07D 281/02
[52] U.S. Cl. ...................................... 540/491
[58] Field of Search .............................. 540/491

[56] References Cited

U.S. PATENT DOCUMENTS

| | | | |
|---|---|---|---|
| 3,089,872 | 5/1963 | Krapcho | 260/239.3 |
| 3,117,124 | 1/1964 | Krapcho et al. | 260/243 |
| 3,166,554 | 1/1965 | Krapcho | 260/243 |
| 3,173,912 | 3/1965 | Krapcho | 260/239.3 |
| 3,341,519 | 9/1967 | Krapcho | 260/239.3 |
| 3,361,750 | 1/1968 | Krapcho | 260/268 |
| 3,361,760 | 1/1968 | Krapcho | 260/327 |
| 3,395,150 | 7/1968 | Krapcho | 260/268 |
| 3,401,166 | 9/1968 | Krapcho | 260/243 |
| 3,441,564 | 4/1969 | Krapcho | 260/244 |
| 3,475,423 | 10/1969 | Krapcho | 260/243 |
| 3,519,647 | 7/1970 | Krapcho | 260/327 |
| 3,535,338 | 10/1970 | Krapcho | 260/327 |
| 3,715,353 | 2/1973 | Krapcho | 260/243 R |
| 3,738,999 | 6/1973 | Krapcho et al. | 260/327 B |
| 3,746,706 | 7/1973 | Krapcho | 260/240 F |
| 3,748,321 | 7/1973 | Krapcho | 260/239 BB |
| 3,763,214 | 10/1973 | Krapcho et al. | 260/470 |
| 3,763,215 | 10/1973 | Krapcho et al. | 260/470 |
| 3,767,653 | 10/1973 | Krapcho | 260/243 R |
| 3,948,889 | 4/1976 | Krapcho et al. | 260/239.3 B |
| 3,953,469 | 4/1976 | Krapcho | 260/333 |
| 3,984,405 | 10/1976 | Krapcho | 260/244 R |
| 4,232,027 | 11/1980 | Krapcho et al. | 424/258 |

OTHER PUBLICATIONS

Price et al, "Relative Reactivities for Monofunctional Nitrogen Mustard Alkylation of Nucleic acid Components" Biochemica et Biophysica Acta vol. 169 pp. 327–359 (1968).

Chemistry Letters (1981) 1143–1146, "N–Alkylation of Amides and N–Heterocycles with Potassium Fluoride on Alumina", J. Yamawaki, et al.

Indian Journal of Chemistry (1973) vol. 11, 234–236, "Studies in Potential Antifertility Agents: Part VI–Synthesis of Dialkylaminoethoxy Derivatives of 3,4-Diphenylcarbostyril, 3,4–Diphenylcinnoline, 2,3-Diphenyl-4-quinazolone & 2,3-diphenylquinooxaline", R. N. Iyer, et al.

Journal of the Chemical Society (1927) 2738, "The Condensation of O–Aminothiophenol with $\alpha\beta$-Unsaturated Acids", W. H. Mills, et al.

*Primary Examiner*—Robert T. Bond
*Attorney, Agent, or Firm*—Jordan B. Bierman, Linda Bierman

[57] ABSTRACT

A benzothiazepine derivative of the formula:

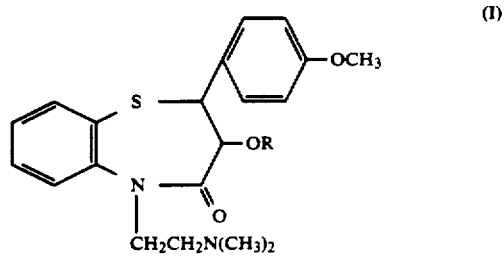

(I)

wherein R is hydrogen or acetyl, is prepared by condensing a compound of the formula:

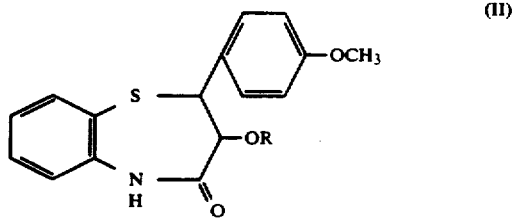

(II)

wherein R is the same as defined above, with 2-(dimethylamino)ethyl halide (i) in the presence of potassium hydroxide in acetone; or (ii) in the presence of potassium carbonate in acetone, lower alkyl acetate, a mixture of acetone and water or a mixture of lower alkyl acetate and water.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

* * * * *